United States Patent
Lisowska et al.

(10) Patent No.: US 11,625,597 B2
(45) Date of Patent: Apr. 11, 2023

(54) MATCHING NETWORK FOR MEDICAL IMAGE ANALYSIS

(71) Applicant: Canon Medical Systems Corporation, Otawara (JP)

(72) Inventors: Aneta Lisowska, Edinburgh (GB); Vismantas Dilys, Edinburgh (GB)

(73) Assignee: Canon Medical Systems Corporation, Otawara (JP)

( * ) Notice: Subject to any disclaimer, the term of this patent is extended or adjusted under 35 U.S.C. 154(b) by 1117 days.

(21) Appl. No.: 16/161,226

(22) Filed: Oct. 16, 2018

(65) Prior Publication Data

US 2019/0147334 A1 May 16, 2019

Related U.S. Application Data

(60) Provisional application No. 62/586,574, filed on Nov. 15, 2017.

(51) Int. Cl.
*G06N 3/08* (2006.01)
*G16H 30/40* (2018.01)
(Continued)

(52) U.S. Cl.
CPC ............ *G06N 3/08* (2013.01); *G06F 16/51* (2019.01); *G16H 30/40* (2018.01); *G16H 50/20* (2018.01); *G16H 50/70* (2018.01)

(58) Field of Classification Search
CPC ...... G06N 3/08; G06N 3/0445; G06N 3/0454; G06N 3/0472; G06N 3/088; G06F 16/51; G16H 30/40; G16H 50/20; G16H 50/70
See application file for complete search history.

(56) References Cited

U.S. PATENT DOCUMENTS 8,751,530 B1 * 6/2014 Ioffe ................. G06F 16/583
707/772
10,037,601 B1 * 7/2018 Ben-Ari ............... A61B 6/5258
(Continued)

FOREIGN PATENT DOCUMENTS

CN 107072613 A * 8/2017 ........... A61B 5/0033
JP 2015-185149 A 10/2015
(Continued)

OTHER PUBLICATIONS

Borg, et al., Modern Multidimensional Scaling; Theory and Applications, Springer Series in Statistics, 2005, Springer-Verlag New York, chapters 1 to 6, 66 pages.
(Continued)

*Primary Examiner* — Xin Jia
(74) *Attorney, Agent, or Firm* — Oblon, McClelland, Maier & Neustadt, L.L.P.

(57) ABSTRACT

The present disclosure is directed to an apparatus and method for data analysis for use in data classification via training of a recurrent neural network to identify features from limited reference sets. Based on a one-shot learning algorithm, the method includes selecting a subset of reference data and training a classifier with the selected data. This small subset of reference data can be iteratively tuned to enhance classification of the data according to the desired output of the method. The apparatus may be configured to allow a user to interactively select a subset of reference data which is used to train the classifier and to evaluate classifier performance.

23 Claims, 13 Drawing Sheets

(51) Int. Cl.
*G16H 50/20* (2018.01)
*G06F 16/51* (2019.01)
*G16H 50/70* (2018.01)

(56) References Cited

U.S. PATENT DOCUMENTS

2015/0254496 A1 9/2015 Nada et al.
2016/0287214 A1 10/2016 Ralovich et al.
2018/0039887 A1* 2/2018 Shaji ............... G06V 20/30

FOREIGN PATENT DOCUMENTS

JP 2016-99734 A 5/2016
JP 2016-133895 A 7/2016
WO WO 2014/133756 A2 9/2014

OTHER PUBLICATIONS

Vinyals, O. et al. "Matching Networks for One Shot Learning" Advances in Neural Information Processing Systems, 2016, 12 pages.
Wickelmaier, F. "An Introduction to MDS" Sound Quality Research Unit, Aalborg University, Denmark, 2003, pp. 1-26.
Van Der Maaten, L. et al. "Visualizing Data using t-SNE" Journal of Machine Learning Research 1, 2008, pp. 1-25.
"t-distributed stochastic neighbor embedding" Wikipedia, https://en.wikipedia.org/wiki/T-distributed_stochastic_neighbor_embedding, 2018, 4 pages.
"Multidimensional scaling" Wikipedia, https://en.wikipedia.org/wiki/Multidimensional_scaling, 2018, 6 pages.
"How to Use t-SNE Effectively" Distill, https://distill.pub/2016/misread-tsne/, 2018, 10 pages.
"Teachable Machine" Google, https://teachablemachine.withgoogle.com/, 2018, 4 pages.
"Search for images with reverse image search" Google, https://support.google.com/websearch/answer/1325808, 2018, 2 pages.
Dspeursinge, A. et al. "Building a reference multimedia database for interstitial lung diseases" Computerized Medical Imaging and Graphics, 2011, pp. 1-12.
Frans, K. "Variational Autoencoders Explained" http://kvfrans.com/variational-autoencoders-explained/, 2016, 7 pages.
Koch, G. "Siamese Neural Networks For One-Shot Image Recognition" Graduate Department of Computer Science, University of Toronto, 2015, Cover Page and pp. 1-27.
Sørensen, L. et al. "Quantitative Analysis of Pulmonary Emphysema Using Local Binary Patterns" IEEE Transactions on Medical Imaging, vol. 29, No. 2, 2010, pp. 559-569.
Taigman, Y. et al. "DeepFace: Closing the Gap to Human-Level Performance in Face Verification" In Proceedings of the IEEE Conference on Computer Vision and Pattern Recognition, 2014, 8 pages.
Japanese Office Action dated Aug. 23, 2022 in Japanese Patent Application No. 2018-214594, 4 pages.

* cited by examiner

|     | P1   | P2   | P3   | P4   | MN   | Vae  | Labels |
|-----|------|------|------|------|------|------|--------|
| MN  | 0.48 | 0.42 | 0.38 | 0.42 |      | 0.52 | 0.54   |
| Vae | 0.50 | 0.28 | 0.38 | 0.40 | 0.52 |      | 0.40   |

Fig. 10

| Training patterns | Test pattern matching agreement | | | | | Total test agreement |
| --- | --- | --- | --- | --- | --- | --- |
| | emphysema | healthy | micronodules | fibrosis | ground glass | |
| emph, fib, gg | | 0.95 | | | | 0.96 |
| nod, fib, gg | 0.84 | 0.97 | 0.97 | | | 0.91 |
| nod, he, fib | 0.94 | | 0.87 | | 0.63 | 0.79 |
| he, fib, gg | 0.66 | 0.90 | | | | 0.76 |
| emph, nod, gg | | 0.75 | | 0.55 | | 0.73 |
| emph, nod, fib | 0.85 | | | 0.49 | 0.66 | 0.70 |
| nod, he, gg | | | 0.63 | | | 0.67 |
| emph, he, fib | | | | | 0.71 | 0.67 |
| emph, he, nod | | | | 0.48 | 0.6 | 0.54 |
| emph, he, gg | | | 0.56 | 0.46 | | 0.51 |

Fig. 11

| Unseen patch patterns | Support set 1 | Support set 5 |
|---|---|---|
| micronodules, ground glass | 0.67 | 0.71 |
| fibrosis, ground glass | 0.65 | 0.67 |
| emphysema, micronodules | 0.60 | 0.67 |
| micronodules, fibrosis | 0.62 | 0.66 |
| healthy, micronodules | 0.63 | 0.66 |
| healthy, fibrosis | 0.58 | 0.64 |
| healthy, ground glass | 0.59 | 0.62 |
| emphysema, fibrosis | 0.60 | 0.61 |
| emphysema, micronodules | 0.58 | 0.61 |

Fig. 13

MATCHING NETWORK FOR MEDICAL IMAGE ANALYSIS

BACKGROUND

Field of the Disclosure

The present disclosure relates to the detection and diagnosis of tissue pathologies. Specifically, the present disclosure describes an apparatus and a method, which use one-shot learning algorithms, to detect and diagnose tissue diseases including, but not limited to, interstitial lung nodule disease, wherein an imbalanced repair response leads to alveolar tissue thickening and poor oxygen diffusion characteristics.

Description of the Related Art

Detection and diagnosis of lung tissue disease can provide clinicians with an opportunity for early intervention and treatment of damaged tissue.

Commonly, computed tomography is employed to aid in the determination of disease state. Interactive segmentation tools afford clinicians the ability to select regions of interest from an image and compare those regions and images with a database of labelled healthy and diseased tissue samples. While simply described, these tools require matching algorithms to be trained on databases of thousands of example tissue samples, building a network of static embeddings that can be cross-referenced with a future query image for classification. While these tools can be effective in specific situations, they are often inflexible, time consuming, or too specialized to a specific disease state to be generally applicable.

Recently, matching algorithms have been developed which are based on one-shot learning, a machine learning paradigm which aims to learn a new concept from a very limited number of training samples. For example, a neural network architecture for one-shot classification relying on image matching has been proposed in an article titled "Matching networks for one shot learning" by Vinyals, et al., published in Advances in Neural Information Processing Systems, 3630-3638, 2016. This article describes the use of ideas from metric learning based on deep neural features and advances that augment neural networks with external memories to learn a network that maps a small labelled support set and an unlabelled example to its label, obviating the need for fine tuning to adapt to new class types. However, such methods may not be sufficiently intuitive, sufficiently flexible or sufficiently practicable to be used by a user who does not possess detailed or expert knowledge of the underlying algorithms.

The foregoing "Background" description is for the purpose of generally presenting the context of the disclosure. Work of the inventors, to the extent it is described in this background section, as well as aspects of the description which may not otherwise qualify as prior art at the time of filing, are neither expressly or impliedly admitted as prior art against the present invention.

BRIEF DESCRIPTION OF THE DRAWINGS

A more complete appreciation of the disclosure and many of the attendant advantages thereof will be readily obtained as the same becomes better understood by reference to the following detailed description when considered in connection with the accompanying drawings, wherein:

FIG. 10 is a tabular representation of accuracy of human observation, a fully supervised matching network, and a fully unsupervised training set-up (variational autoencoder) with respect to true labels;

FIG. 11 is a tabular representation of the performance of a partially supervised matching network in predicting the classification of unseen classes;

FIG. 13 is a tabular representation of the effect of support set size on the performance of the matching network when tested on two unseen cases.

DETAILED DESCRIPTION

Figure 1:
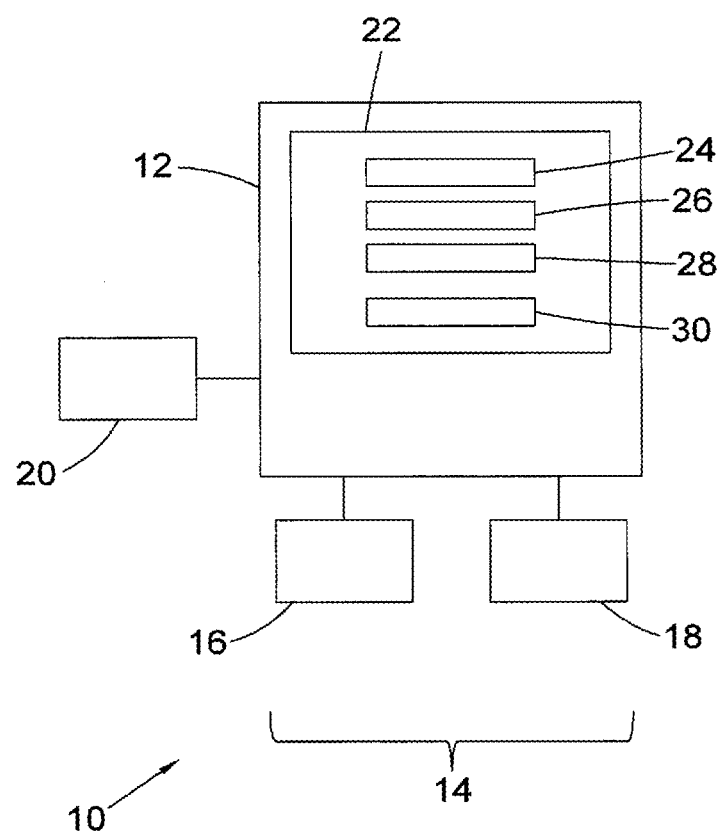
FIG. 1 is an apparatus for data analysis of the present disclosure.

The present disclosure is directed generally to a method for data analysis via training of a process to identify features from limited reference sets. Based on a one-shot learning algorithm, the method, also referred to as a matching network, is related to selecting a subset of reference data and training a classifier with the selected data. This small subset of reference data can be iteratively tuned to enhance classification of the data according to the desired output of the method. The tuning of the reference data may be performed by a user via a user interface and based on a visual representation of the classification that is presented to the user via the user interface. In an exemplary embodiment, the method is further applied to medical images.

Certain embodiments provide an apparatus for data analysis, comprising processing circuitry configured to: select from a set of reference data, a first subset of reference data, each element of the first subset of reference data belonging to a first classification category; select from the set of reference data a second subset of reference data, each element of the second subset of reference data belonging to a second classification category; train a classifier using the first and second subsets of reference data; classify the first and second subsets of reference data using the trained classifier; select from the set of reference data, a subsequent subset of reference data based upon an evaluation of the classification of the first subset of reference data and/or the second subset of reference data; and further train the classifier using the subsequent subset of reference data.

Certain embodiments provide a method, or a non-transitory computer readable medium, comprising a set of instructions, which, when executed by a processing circuitry, cause the processing circuitry to perform a method, the method comprising: selecting from a set of reference data, a first subset of reference data, each element of the first subset of reference data belonging to a first classification category; selecting from the set of reference data a second subset of reference data; training a classifier using the using the first and second subsets of reference data; classifying the first and second subsets of reference data using the trained classifier; selecting from the set of reference data, a subsequent subset of reference data based upon an evaluation of the classification of the first subset of reference data and/or the second subset of reference data; and training the classifier using the subsequent subset of reference data.

The terms "a" or "an", as used herein, are defined as one or more than one. The term "plurality", as used herein, is defined as two or more than two. The term "another", as used herein, is defined as at least a second or more. The terms "including" and/or "having", as used herein, are defined as comprising (i.e., open language). Reference throughout this document to "one embodiment", "certain embodiments", "an embodiment", "an implementation", "an example" or similar terms means that a particular feature, structure, or characteristic described in connection with the embodiment is included in at least one embodiment of the present disclosure. Thus, the appearances of such phrases or in various places throughout this specification are not necessarily all referring to the same embodiment. Furthermore, the particular features, structures, or characteristics may be combined in any suitable manner in one or more embodiments without limitation.

An apparatus for data analysis 10 according to an embodiment is illustrated schematically in FIG. 1. In the present embodiment, the apparatus for data analysis 10 is configured to analyze medical imaging data. In other embodiments, the apparatus for data analysis 10 is configured to analyze any appropriate data.

The apparatus for data analysis 10 comprises a computing apparatus 12, which in this case is a personal computer (PC) or workstation. The computing apparatus 12 is connected to a user interface 14 in the form of a display screen 16 and an input device or devices 18, such as a computer keyboard and mouse. In alternative embodiments, the user interface 14 may be a touch screen which serves as the display screen 16 and the input device 18. In some embodiments, the computing apparatus 12 is a mobile device, for example a smartphone or tablet computer. In some embodiments, the computing apparatus 12 comprises two or more computing devices, which may be configured for communication, for example wired or wireless communication, with one another.

The computing apparatus 12 receives data from a data store 20. In alternative embodiments, the apparatus for data analysis 10 receives data from one or more further data stores (not shown) instead of, or in addition to, the data store 20. For example, the apparatus for data analysis 10 may receive data from one or more remote data stores (not shown) which may form part of a Picture Archiving and Communication System (PACS).

Computing apparatus 12 provides a processing resource or processing circuitry for automatically or semi-automatically processing data in the form of a central processing unit (CPU) 22.

The CPU 22 includes display circuitry 24 configured to display imaging data on display screen 16; category selection circuitry 26 configured to allow a user to define or select a category; region selection circuitry 28 configured to allow a user to select a region of interest of the displayed imaging data; and learning algorithm circuitry 30.

In the present embodiment, the circuitries 24, 26, 28, 30 are each implemented in computing apparatus 12 by means of a computer program which includes computer-readable instructions which, when executed by the CPU 22, cause the apparatus for data analysis 10 to perform a method according to an embodiment. However, in other embodiments, the circuitries 24, 26, 28, 30 may be implemented as one or more ASICs (application specific integrated circuits) or FPGAs (field programmable gate arrays).

The computing apparatus 12 also includes a hard drive and other components of a PC including RAM, ROM, a data bus, an operating system including various device drivers, and hardware devices including a graphics card. In the interests of clarity, such components are not shown in FIG. 1.

Figure 2:
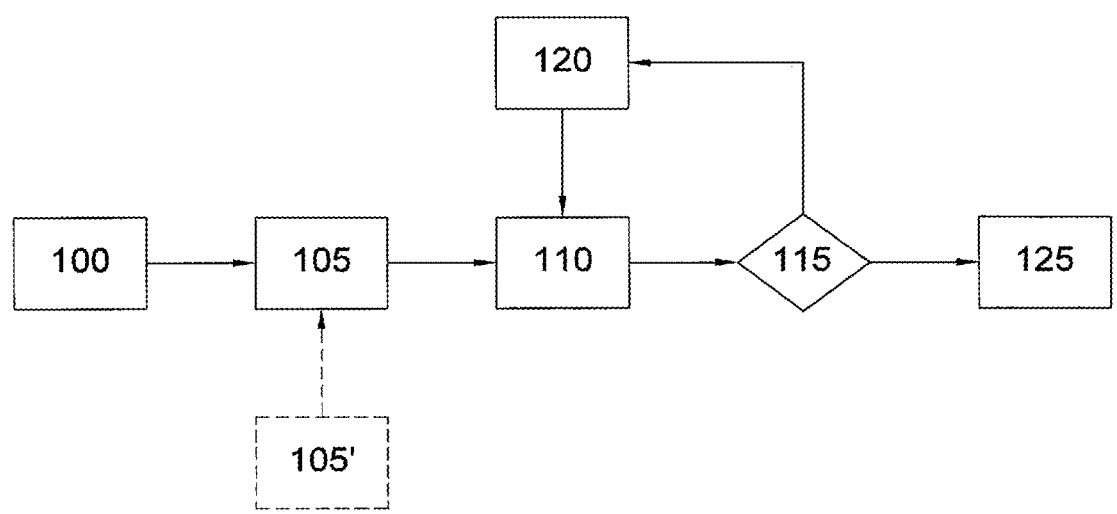
FIG. 2 is a flowchart of a method for data analysis of the present disclosure in the form of a generic embodiment of a method of data classification.

The apparatus for data analysis 10 of FIG. 1 is configured to perform a method for data analysis in the form of a method or algorithm for data classification performed using a matching network trained in supervised fashion to match similar images, as illustrated generically in overview in the flow chart of FIG. 2. As shown in FIG. 2, first, target classification categories of data are selected 100, for example by a user via the user interface 14, the display circuitry 24, and the category selection circuitry 26. Next, a short series of reference data is selected 105 for training a classifier to be applied to unknown query data (e.g., query images), for example by a user via the user interface 14, the display circuitry 24, and the region selection circuitry 28. The learning algorithm circuitry 30 executes a pre-trained one-shot learning algorithm 105' in combination with the short series of reference data. The one-shot learning algorithm 105' employs a deep learning method specifically designed to adjust itself to any problem by using small amounts of data relevant to that problem. After such adjustment, the algorithm can then applied to any desired amount of data, for example to perform a classification with respect to any amount of data. Specifically, the learning algorithm circuitry 30 trains the classifier at 105, using the short series of reference data, and the display circuitry 24 projects the results of the classification of the short series of reference data at 110 into a 2-dimensional or 3-dimensional space on the display screen 16 to illustrate the effectiveness of the trained classifier in classifying the reference data. In this projection, better separation of the reference data with respect to location within quadrants of a graph corresponds to a better classifier. By evaluating the performance of the matching network in real time, modifications (i.e. additions/deletions) can be made to the reference data in real time. The actual classification results are compared with a pre-determined correlation threshold at 115, for example by a user via the display screen 16. If the classification results demonstrate effective classification of the reference data by reaching the pre-determined correlation threshold, the learning algorithm circuitry 30 can apply the trained classifier broadly to a large library of unknown query data at 125 without further training. Alternatively, if classification results illustrate poor classification of the reference data 110, updated reference data are selected at 120, for example by a user via the user interface 14, the display circuitry 24, and the region selection circuitry 28 for training a new classifier. If it is determined at 115 that the resulting classification is effective or accurate, the learning algorithm circuitry 30 applies the newly trained classifier broadly to a large library of unknown query data at 125 without further training. However, if it is determined that the performance of the newly trained classifier is still insufficient or inadequate at 115, training proceeds iteratively until the performance of the classifier is sufficient or adequate.

Figure 3:
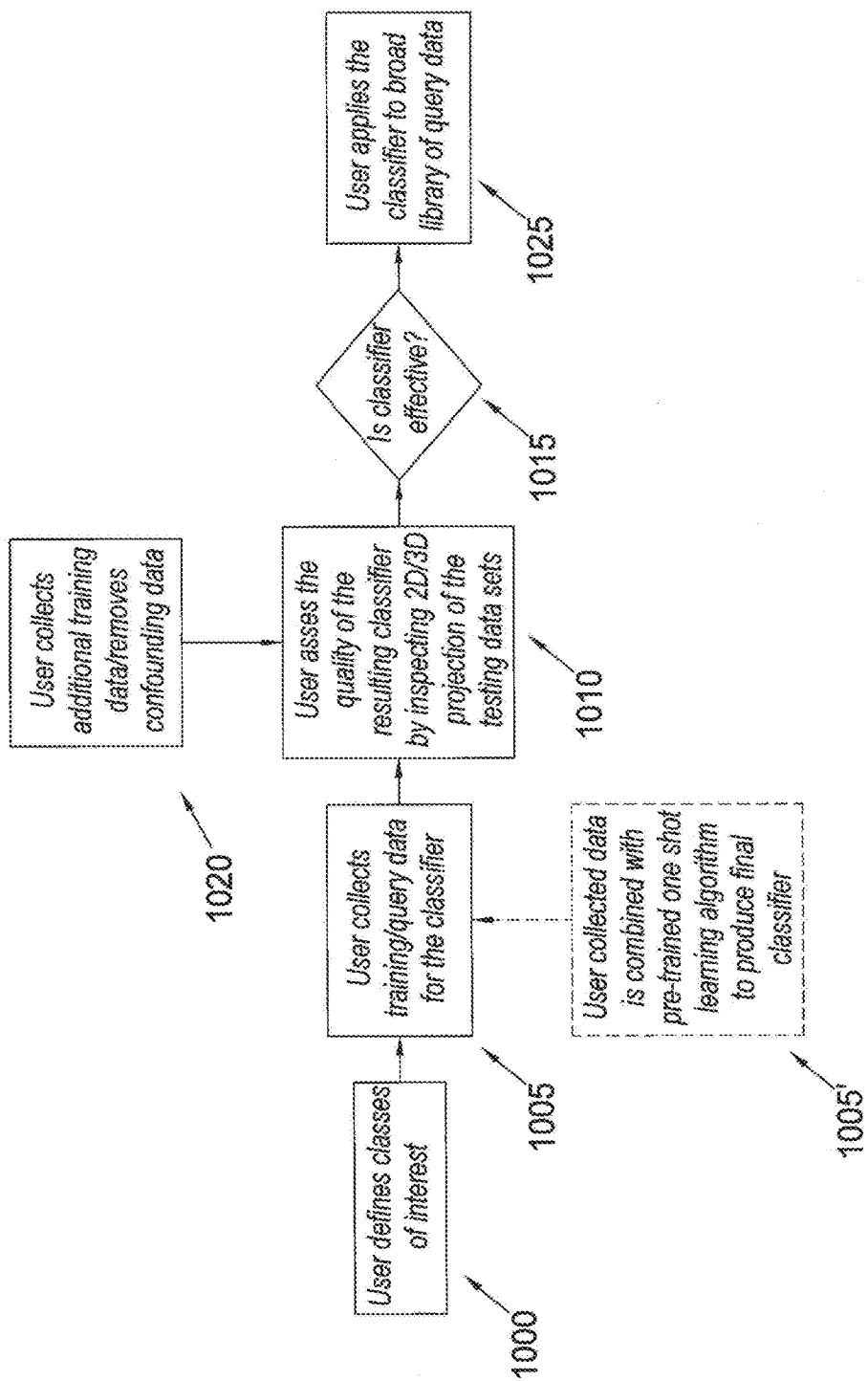
FIG. 3 is a flowchart of a generic, user-guided embodiment of a method for data analysis of the present disclosure in the form of a method of data classification.
Figure 4:
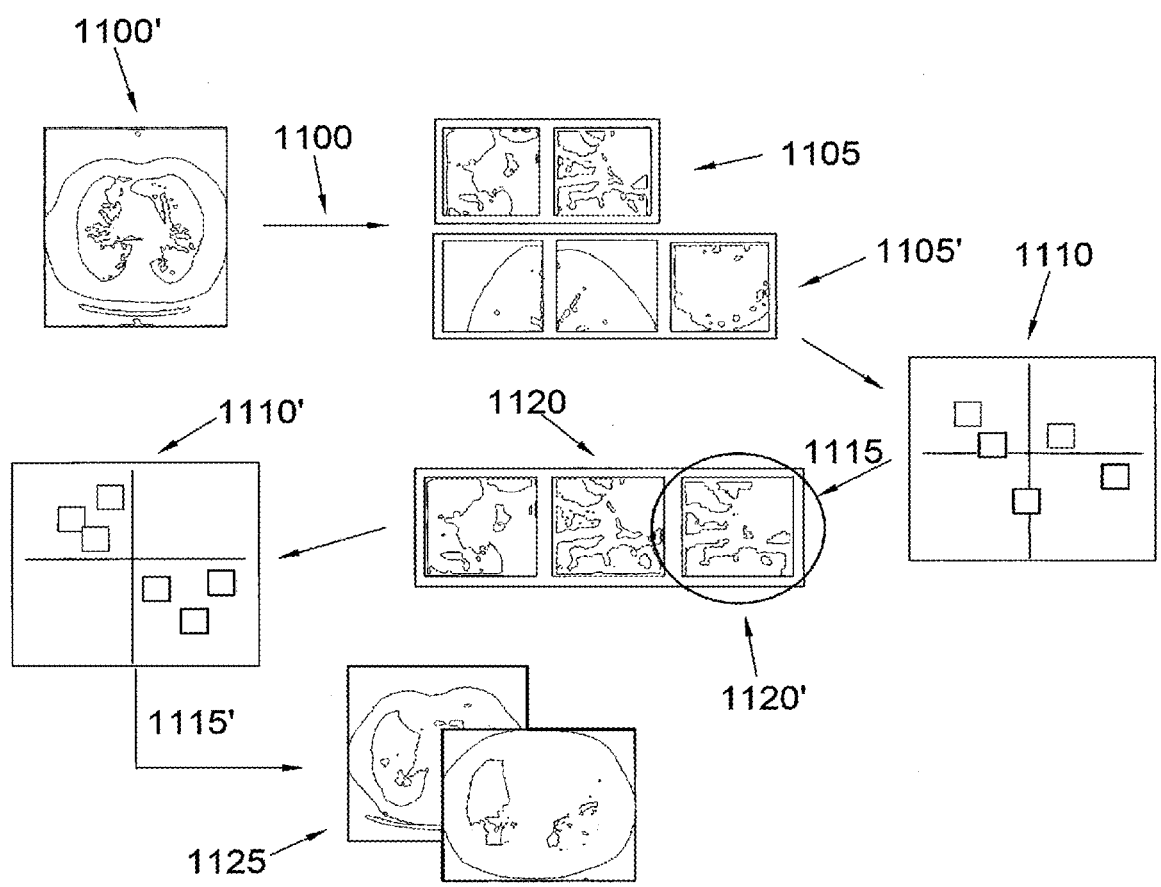
FIG. 4 is a flowchart of an exemplary, user-guided embodiment of a method for data analysis of the present disclosure in the form of a method of data classification.
Figure 5:
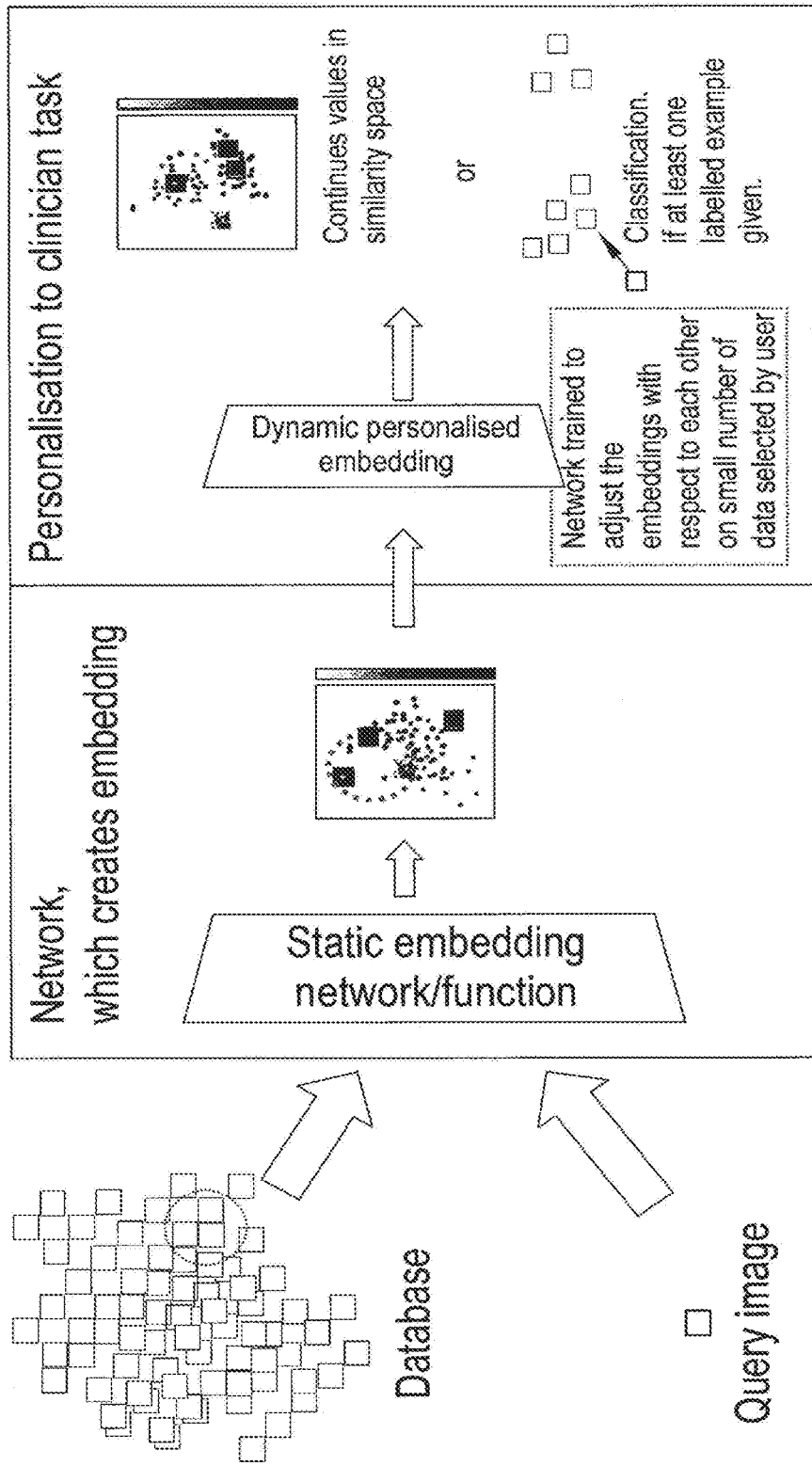
FIG. 5 is an illustration of an embodiment of a method for data analysis of the present disclosure in the form of a similarity search method

Results and teachings from the above-mentioned algorithm development are deployed in FIGS. 3 through 5.

FIG. 3 is a flowchart of a generic, user-guided embodiment of a method of data analysis in the form of a method of data classification. Specifically, the method of FIG. 3 relates to a user-interactive method of classification of medical image data using the apparatus for data analysis 10 of FIG. 1. First, a user selects at 1000 the tissue types, or classification categories, of interest, for example via the user interface 14, the display circuitry 24, and the category selection circuitry 26, wherein the tissue types comprise healthy tissues, diseased tissues and background. These tissue types include, but are not limited to, lung tissue, cardiac tissue, vascular tissue, and skeletal muscle tissue, as well a variety of other soft and hard tissues. Next, the user selects at 1005, for example via the user interface 14, the display circuitry 24, and the region selection circuitry 28, a series of training images for training of a classifier to be applied to unknown query images. Training images can be derived from a variety of medical imaging modalities including, but not limited to computed tomography, X-Ray, magnetic resonance imaging, positron emission tomography, and ultrasound. The learning algorithm circuitry 30 combines the series of training images with a neural network in the form of a pre-trained one-shot learning algorithm 1005' to train the classifier. The learning algorithm circuitry 30 applies the trained classifier at 1005 to the training images and the display circuitry 24 projects the results at 1010 into 2-dimensional space on the display screen 16 to illustrate the effectiveness of the trained classifier in identifying tissue types. This graphical projection of classifier performance allows modifications to the training images to be made in real time, wherein the user determines image correlation via graphical visualization of the images within quadrants of a graph displayed on the display screen 16. If it is determined at 1015 that the results demonstrate effective classification of tissue types (i.e., target classification is visually correlated with classification of the training images on the graph), the learning algorithm circuitry 30 applies the trained classifier broadly to a large library of unknown query images at 1025. Alternatively, if it is determined that the results illustrate poor classification of tissue types at 1025, the user may provide input 1020 via the user-interface 14 to update the training images (e.g. add further training images and/or delete some of the previously selected training images) and the learning algorithm circuitry 30 retrains the classifier at 1020. If it is determined at 1015 that the retrained classifier is effective in classifying the selected tissue types, the learning algorithm circuitry 30 applies the retrained classifier broadly to a large library of unknown query images at 1025.

FIG. 4 is an illustrative flowchart of an exemplary embodiment of a method of data analysis in the form of a method of data classification. In the exemplary embodiment of FIG. 4, the fully supervised matching network method is deployed for user-directed training of a classifier for medical images. First, the display screen 16 of the user-interface 14 displays to a user an example of a reference image set 1100'. Next, at 1100, the user selects first and second classification categories of interest (i.e., micronodules and background) via the user-interface 14. To train the classifier, the user selects, from a set of reference data, a first subset of reference data, each element of the first subset of reference data belonging to the first classification category. The user further selects, from the set of reference data, a second subset of reference data, each element of the second subset of reference data belonging to the second classification category. Specifically, the user initially selects, via the user-interface 14, a small number of reference images representative of the first chosen classification category of interest (i.e. micronodules 1105) and the user initially selects, via the user-interface 14, a small number of reference images representative of the second chosen classification category of interest (i.e. background 1105'). More specifically, the user initially selects, via the user-interface 14, one or more regions of interest of the reference image set 1100' representative of the first chosen classification category of interest (i.e. micronodules 1105) and the region selection circuitry 28 allocates the imaging data associated with each of the selected regions of interest to a corresponding element of the first subset of reference data. In addition, the user initially selects, via the user-interface 14, one or more regions of interest of the reference image set 1100' representative of the second chosen classification category of interest (i.e. background 1105') and the region selection circuitry 28 allocates the imaging data associated with each of the selected regions of interest to a corresponding element of the second subset of reference data.

The learning algorithm circuitry 30 uses the initially selected reference images, in combination with a pre-trained one-shot learning algorithm, to train a classifier. The learning algorithm circuitry 30 uses the trained classifier to classify the first and second subsets of reference data and the display circuitry 24 projects the elements of the first and second subsets of reference data into a 2-dimensional similarity space or graphical representation of correlation 1110 on the display screen 16 in which more similar elements of data are displayed closer together and more dissimilar elements of data are displayed further apart. For example, the display circuitry 24 may use Multi-dimensional Scaling (MDS) to project the elements of the first and second subsets of reference data into the 2-dimensional similarity space or graphical representation of correlation 1110 on the display screen 16. Multi-dimensional Scaling (MDS) is described in "*An Introduction to MDS*", Florian Wickelmaier, Sound Quality Research Unit, Aalborg University, Denmark, May 4, 2003 which is incorporated herein by reference in its entirety. Alternatively, the display circuitry 24 may use Stochastic Neighbor Embedding (SNE), such as t-Distributed SNE (t-SNE), to project the elements of the first and second subsets of reference data into the 2-dimensional similarity space or graphical representation of correlation 1110 on the display screen 16. Stochastic Neighbor Embedding (SNE) and, in particular, t-Distributed SNE (t-SNE) is described in "*Visualizing Data using t-SNE*", Laurens van der Maaten and Geoffrey Hinton, Journal of Machine Learning Research, 1, (2008) 1-48.

The display circuitry 24 also projects a visual indication of correlation in the form of a set of orthogonal axes into the 2-dimensional similarity space on the display screen 16 to allow a user to evaluate the performance of the matching network visually i.e. to allow a user to evaluate visually the classification of the first and second subsets of reference data. Specifically, a user may evaluate the performance of the matching network by comparing the visual representation of the classification of the first and second subsets of reference data against the orthogonal axes. MDS and t-SNE and other similar techniques can be used to map multidimensional feature vectors to a 2D or 3D dimensional space while trying to preserve the structure available in the high dimensional original feature space. This mapping to 2D or 3D enables human to get an idea of the high dimensional feature space (as humans can not grasp beyond 3D). The visual representation of the mapping can only be judged visually and subjectively. In principle a comparison to a threshold could also be performed in the 2D or 3D space, but usually a user will use their own judgement to assess the visual representation of correlation.

Figure 9:
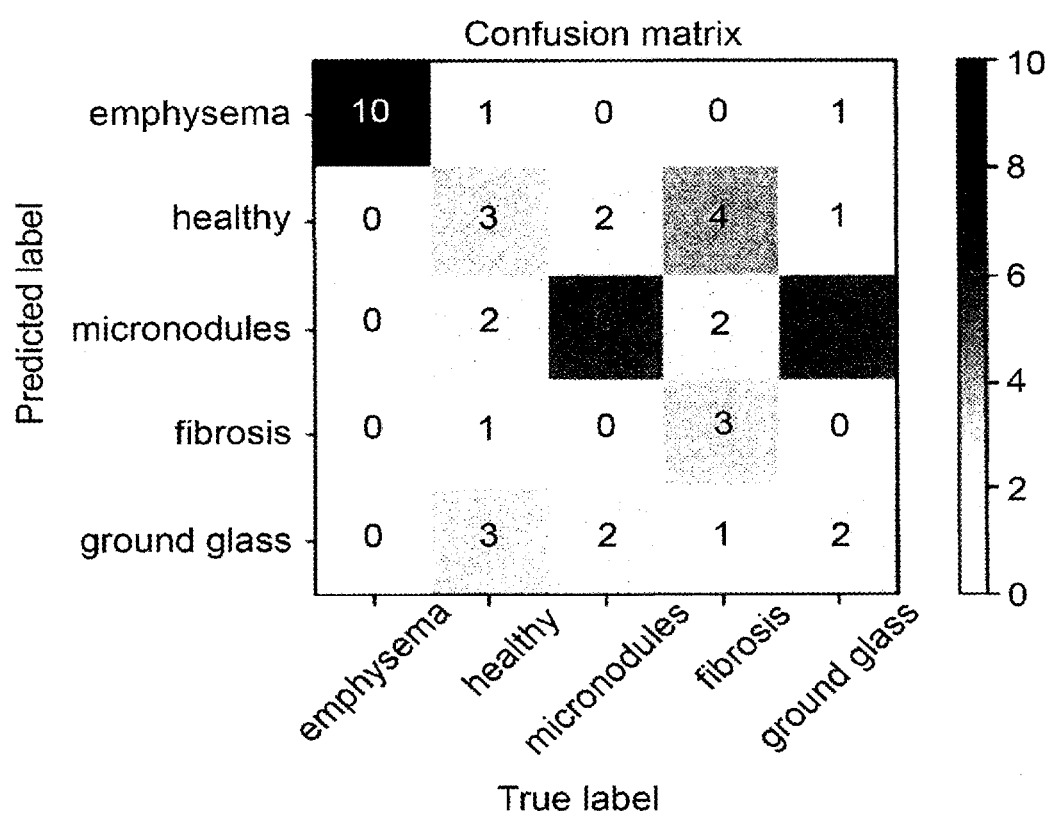
FIG. 9 is a matrix depicting the accuracy of a predicted label with respect to a true label, as determined by a fully unsupervised training set-up.

In the exemplary embodiment shown in FIG. 9, the initially selected reference images are insufficient or inappropriate to train a classifier to correctly separate the initially selected reference images, as reflected by the mis-alignment of the initially selected images of the same classification with respect to different quadrants defined by the orthogonal axes in the graph 1110. In response at 1115, the user selects, from the set of reference data, a subsequent subset of reference data by adjusting the reference images (i.e. the user provides updated reference images 1120 by providing additional reference images and/or deleting reference images) via the user-interface 14 to improve the classifier. In this embodiment, the user selects an additional reference image 1120' representative of tissue containing a micronodule via the user-interface 14. The learning algorithm circuitry 30 then uses the subsequent subset of reference data to retrain the classifier. Specifically, the learning algorithm circuitry 30 uses the updated reference images 1120 to retrain the classifier. The learning algorithm circuitry 30 subsequently applies the retrained classifier to the reference images with the result that all of the reference images belonging to the first classification category appear in one quadrant of the graph 1110' and all of the reference images belonging to the second classification category appear in a different quadrant of the graph 1110', indicating that the retrained classifier has accurately classified the reference images into the selected first and second classification categories.

The learning algorithm circuitry 30 can then apply the retrained classifier to one or more further elements of the set of reference data, or to one or more elements of a further set of reference data, to thereby classify the one or more further elements of the set of reference data, or the one or more elements of the further set of reference data. More specifically, the learning algorithm circuitry 30 can then apply the retrained classifier more broadly at 1115' for classification of unknown query images and large datasets of interest at 1125.

FIG. 5 is an illustration of a method of data analysis in the form of a similarity search method for finding similar examples of a query image in a database of known reference images. In general, in the method of FIG. 10, each element of a first subset of reference data is selected as belonging to a first classification category according to whether each element of the first subset of reference data is similar to a query data element, each element of a second subset of reference data is selected as belonging to a second classification category according to whether each element of the second subset of reference data is dissimilar to the query data element and the first and second subsets of reference data are used to train a classifier. The trained classifier is then used to perform a similarity search of the set of reference data, or of a further set of reference data, based on a further query data element to find one or more further elements in the set of reference data, or one or more elements in the further set of reference data, which are similar to the further query data element.

More specifically, in the method of FIG. 5, first, the learning algorithm circuitry 30 creates static embeddings for each candidate image, for example candidate images selected by a user from a database of known reference images. Next, the static embeddings are then adjusted jointly to create dynamic embeddings, for example based on user input. The user input may comprise, in one example, a user selecting from the set of candidate images via the user interface 14, a candidate image which is considered to be similar to the query image and a candidate image which is considered to be dissimilar to the query image. The learning algorithm circuitry 30 can then, for example, use the selected similar and dissimilar candidate images to determine or modify a dynamic embedding for a tailored similarity search which is adapted according to the user's perception of similarity. The learning algorithm circuitry 30 can then, for example, be used to perform a tailored similarity search of the database of known reference images to find one or more similar images in the database of known reference images which are similar to a further query image. Then, either (1) the display circuitry 24 presents the similar images in a 2-dimensional similarity space via the display screen 16 or (2) the learning algorithm circuitry 30 classifies the similar images i.e. matches the similar images to a known or labelled classification associated with the further query image.

Any suitable learning algorithms or matching network algorithms may be used to implement the methods of the embodiments of FIGS. 2 to 5. Further description is now provided, with reference to FIGS. 6-13, relating to the development and validation of a fully supervised matching network algorithm. It will be understood that any suitable matching network algorithms may be used and embodiments are not limited to the user of algorithms described, developed or referred to in connection with FIGS. 6 to 13. The description relating to FIGS. 6 to 13 examines the inter-observer variability in observers' judgement of similarity versus matching network to match pathology patches trained on ground truth provided to clinicians.

Example images or image patches of four different pathological lung conditions and one healthy lung condition were extracted from two publicly available interstitial lung disease databases. Labelled image patches containing fibrosis, ground glass, micronodules, emphysema and healthy tissue were extracted. Prior to algorithm development, the data was randomly split into a training set and a validation set, approximately balancing the number of patients in each class. Subsequent image patches of 20×20 mm, with 80% overlap, were extracted at 1 mm/pixel resolution. Patch size, overlap, and resolution are non-limiting and evaluated here as a specific embodiment of the disclosure. Patches were fully contained within the labelled ground truth regions.

Figures 6A, 6B:
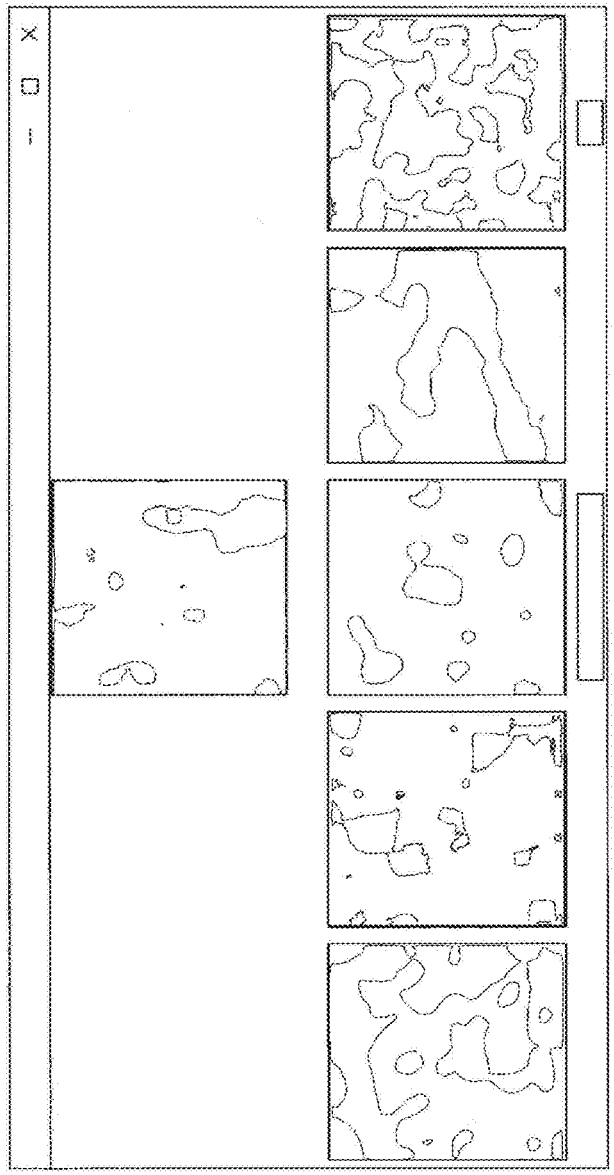
FIG. 6A is an illustration of a user interface configured to determine inter-observer variability in patch selection.
FIG. 6B is a tabular representation of inter-observer variability in pattern similarity matching.

Initially, human similarity perception was evaluated. 100 patches from the patch validation set were used to evaluate how well human non-experts matched categorical labels in comparison to a fully supervisedmatching network method. Each participant matched ten images per pattern category to one of the images from a subset of five selected pattern categories. The same combination of patches was shown to all participants. The experimental set up in FIG. 6A illustrates how each observer was asked to select an image from the bottom row that most closely matches the image patch displayed in the top row. The ability to correlate these images correctly is reflected in FIG. 6B, a tabular representation of the correlation values between observers. In FIG. 6B, P1 to P4 are observers and correlation values reflect inter-observer agreement as well as the agreement between a single observer and the true categorical label.

Figure 7:
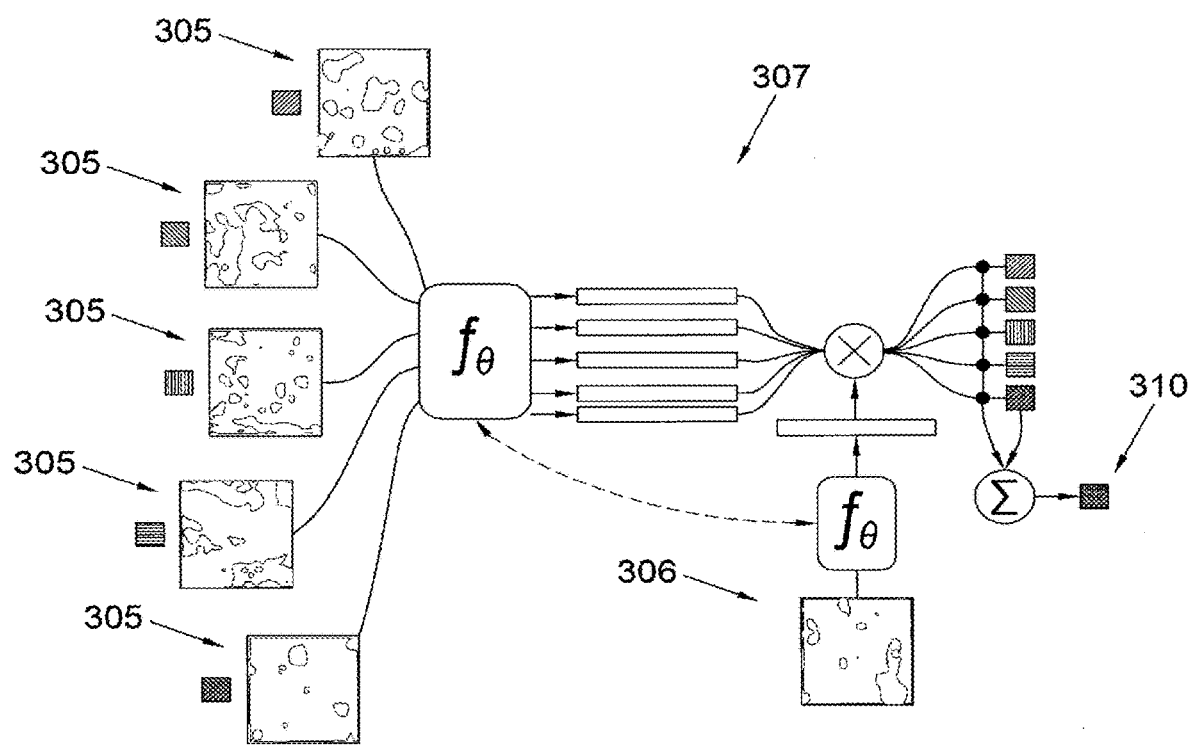
FIG. 7 is an illustration representing a fully supervised matching network, wherein an embedding function is learned on all pattern classes from a training patch set for use in the method of FIG. 2.
Figure 8:
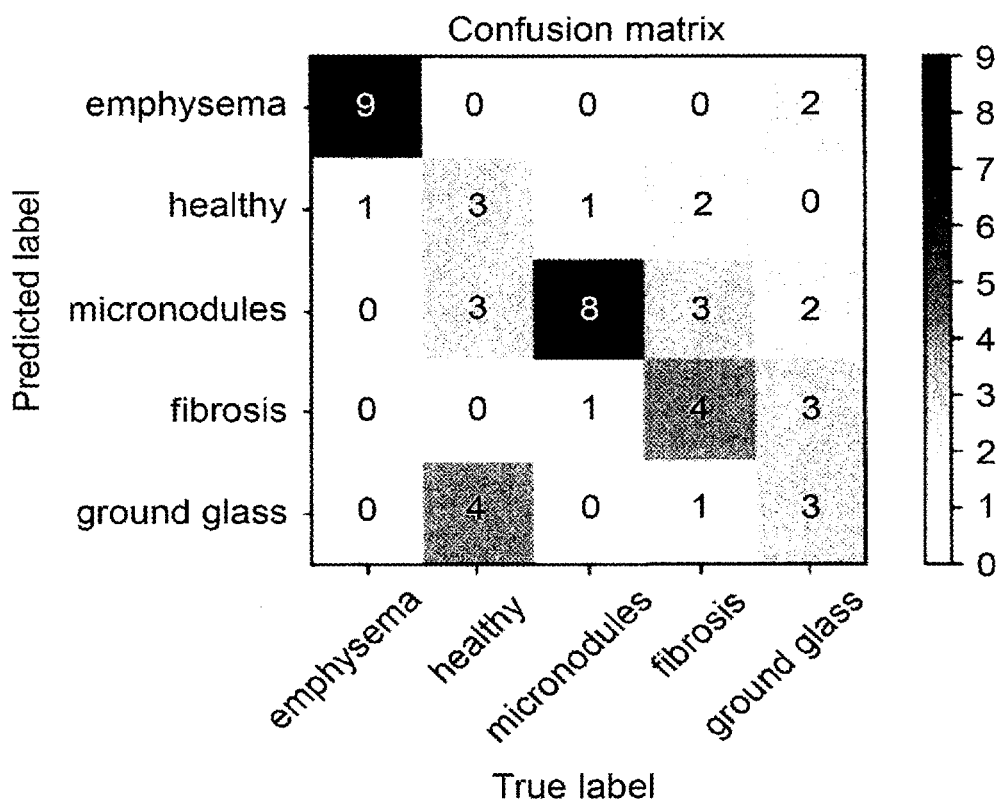
FIG. 8 is a matrix depicting the accuracy of a predicted label with respect to a true label, as determined using the fully supervised matching network of FIG. 7.

In developing the matching network of the present disclosure, a matching network was trained in a fully supervised manner on 10,000 training sets to map a target patch with a patch from one of five classifications. Each training set consisted of five examples from each class and a target class. An embedding function was trained to extract features and, simultaneously, a Recurrent Neural Network learned to select a matching patch. This fully supervised network is illustrated in FIG. 7 which is adapted from FIG. 1 of Vinyals, et al., published in Advances in Neural Information Processing Systems, 3630-3638, 2016. The matching network 307 is trained on multiple training sets 305, each training set consisting of a small number of training examples. An embedding function is learned on all pattern classes from the training sets. Following training, a query image 306 can be matched and classified 310. The trained matching network was evaluated on the small data subset used for evaluation of human perception. FIG. 8 is a matrix illustrating the accuracy of the trained matching network compared with true categorical labels, with darker blue indicating higher correlation of the predicted label with the true label. Emphysema and micronodules appear most easily detected.

As comparison, an embedding function generated using a fully unsupervised training set-up was compared to human perception and the fully supervised matching network. For the fully unsupervised training set-up, an encoding aspect of a trained variational autoencoder (vae) was used to embed the images into a compressed feature space. A Recurrent Neural Network was not used for matching of the images. Instead, simple Euclidian distance between compressed vectors of candidate images and the query image was used to match the query patch to the most similar patch. FIG. 9 is a matrix illustrating the accuracy of the unsupervised training set-up compared with true categorical labels, with dark blue indicating higher correlation of the predicted label with the true label. Emphysema appears most easily detected.

FIG. 10 is a tabular representation of the performance of each matching modality: human perception (P1-P4), supervised matching network (MN), and unsupervised training set-up (Vae). The supervised matching network (MN) displays superior performance in predicting matching of query images with correctly labeled images (Labels).

In a further experiment, the supervised matching network was trained on three image patch categories and tested with two previously unseen image patch categories to evaluate the extent to which the embedding is useful for similarity matching of unseen image patch categories. 10,000 training examples and 600 validation examples were used. At test time, the supervised matching network is required to match a query image patch to one of two unseen image patch categories and the supervised matching network is provided with a single randomly selected example image patch from each class (i.e. the size of the support set is 1). FIG. 11 provides a tabular representation of the performance of the partially supervised matching network in predicting the classification of unseen classes, wherein emph, he, nod, fib, and gg correspond to emphysema, healthy, micronodules, fibrosis, and ground glass, respectively. Variability was present in the effectiveness of the matching network, largely dependent on which patch patterns were selected as training. Test patterns demonstrated poor matching agreement when emphysema, healthy, and ground glass examples are used for training, while matching agreement was high when emphysema, fibrosis, and ground glass examples are used for training.

Figures 12A, 12B:
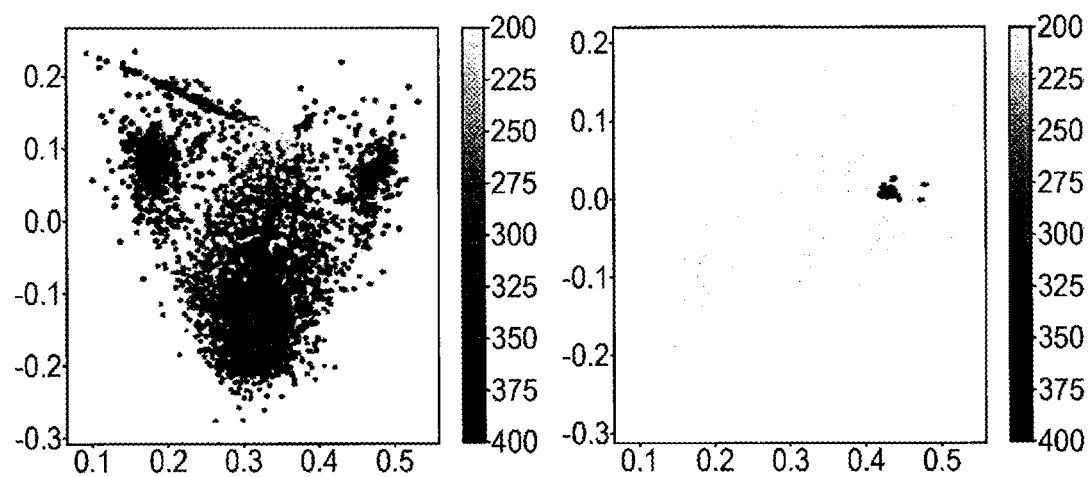
FIG. 12A is a graphical representation of embedding performance, in the context of two unseen cases (healthy, micronodules), as represented by compressed vectors of the training samples.
FIG. 12B is a graphical representation of embedding performance, in the context of two unseen cases (fibrosis, micronodules), as represented by compressed vectors of the training samples.

To better understand the differences between the best and worst performing set-up, the results, displayed as compressed vectors, are projected into a 2-dimensional (2D) similarity space for visualization. The training classes were fed through an embedding function and the output compressed vector was projected into the 2D similarity space using Multi-dimensional Scaling (MDS). FIG. 12A is the resulting 2-dimensional graphical projection of the compressed representation of training examples from the optimal training arrangement, wherein 0 equals emphysema, 1 equals fibrosis, and 2 equals ground glass. FIG. 12B is the resulting 2-dimensional graphical projection of the compressed representation of training examples from the poorest training arrangement, wherein 0 equals emphysema, 1 equals healthy, and 2 equals ground glass.

FIG. 13 is a tabular representation of an investigation into the effect of support set size on the performance of the matching network. In this investigation, the matching network was trained on three image patch classes, learning to map a query image patch to a single image patch class from one of the three image patch classes. During testing, the matching network was required to match a query image patch to one of five image patch classes, wherein two of these classes were previously unseen. To this end, one example image patch was provided from each class when the support set was one, while five example patches were provided from each class when the support set was five. 10,000 training examples and 600 testing examples were used. The example patches from each patch class were randomly selected. The size of the accuracy values shown in FIG. 9 demonstrate that matching network performance improved as support set size increased.

According to an aspect or an embodiment of the present disclosure there is provided a method, comprising: selecting a target classification category; selecting, from a set of reference data, a first subset of reference data, each element of the first subset of reference data belonging to the selected classification category; training a classifier using the first subset of reference data; classifying the first subset of reference data using the trained classifier; selecting, from the set of reference data, a subsequent subset of reference data based upon an evaluation of the classification of the first subset of reference data; and training the classifier using the subsequent subset of reference data.

The method may further comprise evaluating the classification of the first subset of reference data to obtain the evaluation based upon a correlation between the selected classification category and the classification of the first subset of reference data.

The first training step may comprise iteratively training the classifier until the correlation of the selected classification category with the classification of the first subset of reference data reaches a pre-determined correlation threshold.

Each training step may comprise training the classifier using a pre-trained one-shot learning algorithm.

The method may further comprise: selecting another target classification category; selecting, from the set of reference data, a second subset of reference data, each element of the second subset of reference data belonging to the another target classification category; and training the classifier using the first and second subsets of reference data.

The method may further comprise obtaining partial medical images, full medical images, or a combination thereof as the reference data.

The method may further comprise performing a similarity search by applying a query data to the trained classifier using a predetermined database.

According to an aspect or an embodiment of the present disclosure there is provided an apparatus, comprising: a memory to store a plurality of reference data; and processing circuitry configured to select a target classification category; select, from a set of reference data, a first subset of reference data, each element of the first subset of reference data belonging to the selected classification category; train a classifier using the first subset of reference data; classify the first subset of reference data using the trained classifier; select, from the set of reference data, a subsequent subset of reference data based upon an evaluation of the classification of the first subset of reference data; and train the classifier using the subsequent subset of reference data.

The processing circuitry may be further configured to evaluate the classification of the first subset of reference data to obtain the evaluation based upon a correlation between the selected classification category and the classification of the first subset of reference data.

The processing circuitry may be further configured to iteratively train the classifier until the correlation of the selected classification category with the classification of the first subset of reference data reaches a pre-determined correlation threshold.

The processing circuitry may be further configured to train the classifier using a pre-trained one-shot learning algorithm.

The processing circuitry may be further configured to: select another target classification category; select, from the set of reference data, a second subset of reference data, each element of the second subset of reference data belonging to another target classification category; and train the classifier using the first and second subsets of reference data.

The processing circuitry may be further configured to obtain partial medical images, full medical images, or a combination thereof as the reference data.

The processing circuitry may be further configured to perform a similarity search by applying query data to the trained classifier using a predetermined database.

The processing circuitry may be further configured to: cause a display to display a user interface to receive, from the user, selection of the first subset of reference data and selection of the subsequent subset of reference data; and receive and display the plurality of reference data.

According to an aspect or an embodiment of the present disclosure there is provided a non-transitory computer-readable medium, comprising a set of instructions, which, when executed by a processing circuitry, cause the processing circuitry to perform a method, comprising: selecting a target classification category; selecting, from a set of reference data, a first subset of reference data, each element of the first subset of reference data belonging to the selected classification category; training a classifier using the first subset of reference data; classifying the first subset of reference data using the trained classifier; selecting, from the set of reference data, a subsequent subset of reference data based upon an evaluation of the classification of the first subset of reference data; and training the classifier using the subsequent subset of reference data.

The method may further comprise evaluating the classification of the first subset of reference data to obtain the evaluation based upon a correlation between the selected classification category and the classification of the first subset of reference data.

The method may further comprise iteratively training the classifier until the correlation of the selected classification category with the classification of the first subset of reference data reaches a pre-determined correlation threshold.

The method may further comprise training the classifier using a pre-trained one-shot learning algorithm.

The method may further comprise: selecting another target classification category; selecting, from the set of reference data, a second subset of reference data, each element of the second subset of reference data belonging to another target classification category; and training the classifier using the first and second subsets of reference data.

According to an aspect or an embodiment of the present disclosure there is provided a method for the analysis of medical data, the method comprising: visually presenting medical data to a user; allowing the user to select a plurality of samples of the medical data, the plurality of samples belonging to two or more classes of the medical data and each sample exemplifying one of the two or more classes of the medical data; training a classifier to distinguish the two or more classes from the selected plurality of samples; displaying feedback to the user regarding the quality of the classifier; allowing the user to edit the plurality of samples; retraining the classifier using the edited plurality of samples; and displaying feedback to the user regarding the quality of the retrained classifier.

The method may comprise applying the classifier to the medical data or to further medical data to classify the medical data or the further medical data. The method may comprise applying the classifier to the medical data or to the further medical data to segment the medical data or the further medical data. The method may comprise applying the classifier to the medical data or to the further medical data to detect or identify at least one of a condition, a feature, and a disease. The method may comprise applying the classifier to perform a similarity search. The method may comprise displaying the results of the application of the classifier to the medical data or the further medical data. The method may comprise training the classifier with a one-shot approach. The feedback displayed to the user regarding the quality of the classifier may be a 2D or 3D projection of a separation of the classes. The medical data may comprise non-imaging data. The medical data may comprise imaging data. Allowing the user to select a plurality of samples of the medical data may comprise allowing the user to identify a region of interest of the imaging data and selecting the plurality of samples according to the identified region of interest. The region of interest may comprise, or be defined by, at least one of a contour, an image patch, and a whole volume of the imaging data. The method may comprise selecting the samples according to the patient, for example, according to an identity of the patient and/or by patient identification. The method may comprise allowing the user to interact with the displayed feedback to edit the plurality of samples. The method may comprise allowing the user to interact with the displayed feedback to remove one or more of the samples. The method may comprise accumulating the medical data. The method may comprise providing the medical data from a relevant existing database.

According to an aspect or embodiment there is provided a medical image processing apparatus comprising: a memory to store a plurality of supervised data which associated with a classification result;
processing circuitry configured to:
acquire classification target data,
display at least a part of the supervised data which include the classification result based on classification order for the classification target data,
update a classifier concerning the classification target data by accepting an addition or a delete order of the supervised data by user,
process a processing relating to the classification of the classification target data based on the updated classifier.

The processing circuitry may further display a classifying result of updated supervised data based on the updated classifier.

First Embodiment

According to an aspect or embodiment there is provided a
medical image processing apparatus comprising:
a memory to store a plurality of supervised images associated with body part information, wherein the supervised images are partial area images of a medical image;
processing circuitry configured to:
acquire information relating to a plurality of subject's body part by user input,
display the plurality of supervised image which have related body part information based on the information relating to a plurality of subject's body part,
update a classifier of the supervised image relating to the body part by accepting an addition or a delete order of the supervised image to the displayed plurality of supervised image.

The processing circuitry may be further configured to: acquire a medical image of the subject, process a segmentation procedure to the acquired image data in each of the part based on the updated classifier.

According to an aspect or embodiment there is provided a medical image processing apparatus comprising:
a memory to store a plurality of supervised images associated with part information, wherein the supervised images are partial area images of medical image;
processing circuitry configured to:
acquire a query image of subject by user,
display the plurality of supervised image which have related part information based on the query image,
update a classifier of the supervised image relating to the query image by accepting an addition or delete order of the supervised image to the displayed plurality of supervised image.

The processing circuitry may be further configured to: classify the query image according to part of the subject or case based on the updated classifier.

The processing circuitry may be further configured to: calculate a similarity of the query image based on the updated classifier.

One of ordinary skill in the art will understand that numerous modifications and variations are possible in light of the above teachings. It is therefore to be understood that within the scope of the appended claims, the invention may be practiced otherwise than as specifically described herein.

Thus, the foregoing discussion discloses and describes merely exemplary embodiments of the present invention. As will be understood by those skilled in the art, the present invention may be embodied in other specific forms without departing from the spirit or essential characteristics thereof. Accordingly, the disclosure of the present invention is intended to be illustrative, but not limiting of the scope of the invention, as well as other claims. The disclosure, including any readily discernible variants of the teachings herein, defines, in part, the scope of the foregoing claim terminology such that no inventive subject matter is dedicated to the public.

The invention claimed is:

1. An apparatus for data analysis, comprising processing circuitry configured to:
select from a set of reference data, a first subset of reference data, each element of the first subset of reference data belonging to a first classification category;
select from the set of reference data a second subset of reference data;
train a classifier using the first and second subsets of reference data to obtain a first trained classifier;
classify the first and second subsets of reference data using the first trained classifier;
select from the set of reference data, a subsequent subset of reference data based upon an evaluation of the classification of the first subset of reference data and/or the second subset of reference data; and
retrain the first trained classifier using the subsequent subset of reference data to obtain a second trained classifier.

2. The apparatus of claim 1, wherein at least one of a), b):
a) each element of the second subset of reference data belonging to a second classification category;
b) each element of each subsequent subset of reference data belongs to the first classification category or the second classification category.

3. The apparatus of claim 1, wherein the processing circuitry is configured to train the classifier using a one-shot learning algorithm.

4. The apparatus of claim 1, wherein the processing circuitry is configured to cause a display a user interface, the user interface being configured to at least one of a), b), c):
a) receive from a user a selection or definition of the first classification category and/or a second classification category;
b) receive from a user a selection of the first subset of reference data and/or selection of the subsequent subset of reference data;
c) allow a user to evaluate the classification of the first subset of reference data and/or the second subset of reference data to obtain the evaluation of the classification of the first subset of reference data and/or the second subset of reference data.

5. The apparatus of claim 4, wherein the set of reference data comprises medical imaging data, and wherein the user interface is configured to:
display at least a portion of the imaging data;
allow a user to select one or more regions of interest of the imaging data.

6. The apparatus of claim 5, wherein the processing circuitry is configured to allocate the imaging data associated with each selected region of interest to a corresponding element of the first subset of reference data or the second subset of reference data.

7. The apparatus of claim 1, wherein the evaluating of the classification of the first subset of reference data and/or the second subset of reference data comprises:

generating a visual representation of the classification of the first subset of reference data and/or the second subset of reference data, the visual representation being for evaluation by a user.

8. The apparatus of claim 7, wherein the processing circuitry is configured to generate the visual representation of the classification of the first subset of reference data and/or the second subset of reference data by projecting each element of the first subset of reference data and/or the second subset of reference data into a 2D or 3D similarity space in which more similar elements are located closer together and more dissimilar elements are located further apart.

9. The apparatus of claim 8, wherein a pre-determined classifier performance threshold is defined by a 2D or 3D region of the 2D or 3D similarity space or a 2D or 3D boundary of a 2D or 3D region in the 2D or 3D similarity space.

10. The apparatus of claim 8, wherein the processing circuitry is configured to generate the visual representation of the classification of the first subset of reference data and/or the second subset of reference data using at least one of Multi-Dimensional Scaling (MDS); Stochastic Neighbor Embedding (SNE); t-Distributed SNE (t-SNE).

11. The apparatus of claim 1, wherein the processing circuitry is configured to apply the trained classifier to one or more further elements of the set of reference data, or to one or more elements of a further set of data, to thereby classify the one or more further elements of the set of reference data or the one or more elements of the further set of data.

12. The apparatus of claim 1, wherein the processing circuitry is configured to obtain partial medical images, full medical images, or a combination thereof as the reference data.

13. The apparatus of claim 1, wherein the processing circuitry is configured to perform a similarity search by applying query data to the trained classifier.

14. The apparatus of claim 13, wherein the processing circuitry is configured to perform the similarity search by using the trained classifier with respect to a predetermined database to find one or more data elements in the database that are similar to the query data.

15. The apparatus of claim 1, wherein training the classifier comprises training a neural network.

16. The apparatus of claim 1, wherein the evaluation of the classification of the first subset of reference data is based upon a correlation between the first classification category and the classification of the first subset of reference data; and/or is based upon or a comparison against a pre-determined correlation threshold of a correlation of the classification of the first subset of reference data with the first classification category.

17. The apparatus of claim 1, wherein the processing circuitry is further configured to iteratively train the classifier until a correlation of the first classification category with the classification of the first subset of reference data reaches a pre-determined correlation threshold.

18. Apparatus according to claim 1, wherein the selecting of the first subset of reference data, the selecting of the second subset of reference data and the subsequent subset of reference data comprises selecting by a user of the first subset of reference data, the selecting of the second subset of reference data and the subsequent subset of reference data.

19. The apparatus of claim 1, wherein to select the subsequent subset of reference data from the set of reference data, the processing circuitry is configured to:
evaluate the classification of the first subset of reference data to obtain the evaluation by performing a correlation between the first classification category and the classification of the first subset of reference data.

20. A method, comprising:
selecting from a set of reference data, a first subset of reference data, each element of the first subset of reference data belonging to a first classification category;
selecting from the set of reference data a second subset of reference data;
training a classifier using the using the first and second subsets of reference data to obtain a first trained classifier;
classifying the first and second subsets of reference data using the first trained classifier;
selecting from the set of reference data, a subsequent subset of reference data based upon an evaluation of the classification of the first subset of reference data and/or the second subset of reference data; and
retraining the first trained classifier using the subsequent subset of reference data to obtain a second trained classifier.

21. The method of claim 20, wherein selecting the subsequent subset of reference data from the reference data comprises:
evaluating the classification of the first subset of reference data to obtain the evaluation by performing a correlation between the selected classification category and the classification of the first subset of reference data.

22. A non-transitory computer readable medium, comprising a set of instructions, which, when executed by a processing circuitry, cause the processing circuitry to perform a method, comprising:
selecting from a set of reference data, a first subset of reference data, each element of the first subset of reference data belonging to a first classification category;
selecting from the set of reference data a second subset of reference data;
training a classifier using the using the first and second subsets of reference data to obtain a first trained classifier;
classifying the first and second subsets of reference data using the first trained classifier;
selecting from the set of reference data, a subsequent subset of reference data based upon an evaluation of the classification of the first subset of reference data and/or the second subset of reference data; and
retraining the first trained classifier using the subsequent subset of reference data to obtain a second trained classifier.

23. The non-transitory computer readable medium of claim 22, wherein selecting the subsequent subset of reference data from the reference data comprises:
evaluating the classification of the first subset of reference data to obtain the evaluation by performing a correlation between the selected classification category and the classification of the first subset of reference data.

* * * * *